United States Patent [19]

Segal et al.

[11] Patent Number: 4,676,980

[45] Date of Patent: Jun. 30, 1987

[54] TARGET SPECIFIC CROSS-LINKED HETEROANTIBODIES

[75] Inventors: David M. Segal, Rockville; Pilar Perez, Bethesda, both of Md.

[73] Assignee: The United States of America as represented by the Secretary of the Department of Health and Human Services, Washington, D.C.

[21] Appl. No.: 778,670

[22] Filed: Sep. 23, 1985

[51] Int. Cl.⁴ .................... G01N 33/54; G01N 33/58; G01N 33/60
[52] U.S. Cl. ....................................... 424/85; 424/88; 530/387
[58] Field of Search ..................... 424/85, 88; 530/387

[56] References Cited

U.S. PATENT DOCUMENTS 4,048,298  9/1977  Niswender ........................ 436/531
4,433,059  2/1984  Chang et al. ...................... 436/512
4,490,473 12/1984  Brunhouse ........................ 424/85

OTHER PUBLICATIONS

Staerz et al. (1985) Nature 314:628–631.
Kranz et al. (1984) Proc. Natl. Acad. Sci. Immun. 81:7922–7926.
Hoffman et al. (1985) Journ. of Immun. 135:1–4.
Lancki, et al. (1984) Immun. Reviews No. 80, 65–94.
Karpovsky et al. (1984) Journ. of Experim. Med. 160:1686–1701.

Primary Examiner—John Kight
Assistant Examiner—Nathan M. Nutter
Attorney, Agent, or Firm—Holman & Stern

[57] ABSTRACT

The present invention discloses a target specific cross-linked heteroantibody and a method of producing the same. The cross-linked heteroantibodies of the present invention can cause normal autologous cells of the immune system to destroy any unwanted cell for which an antibody is available. Treatment or control of tumors, viral infected cells, fungi, bacteria, parasites and the like is now made possible through the use of the heteroantibody complex of the present invention.

6 Claims, 1 Drawing Figure

CROSS LINKING OF ANTI-T3
WITH ANTI-H-2K$^K$

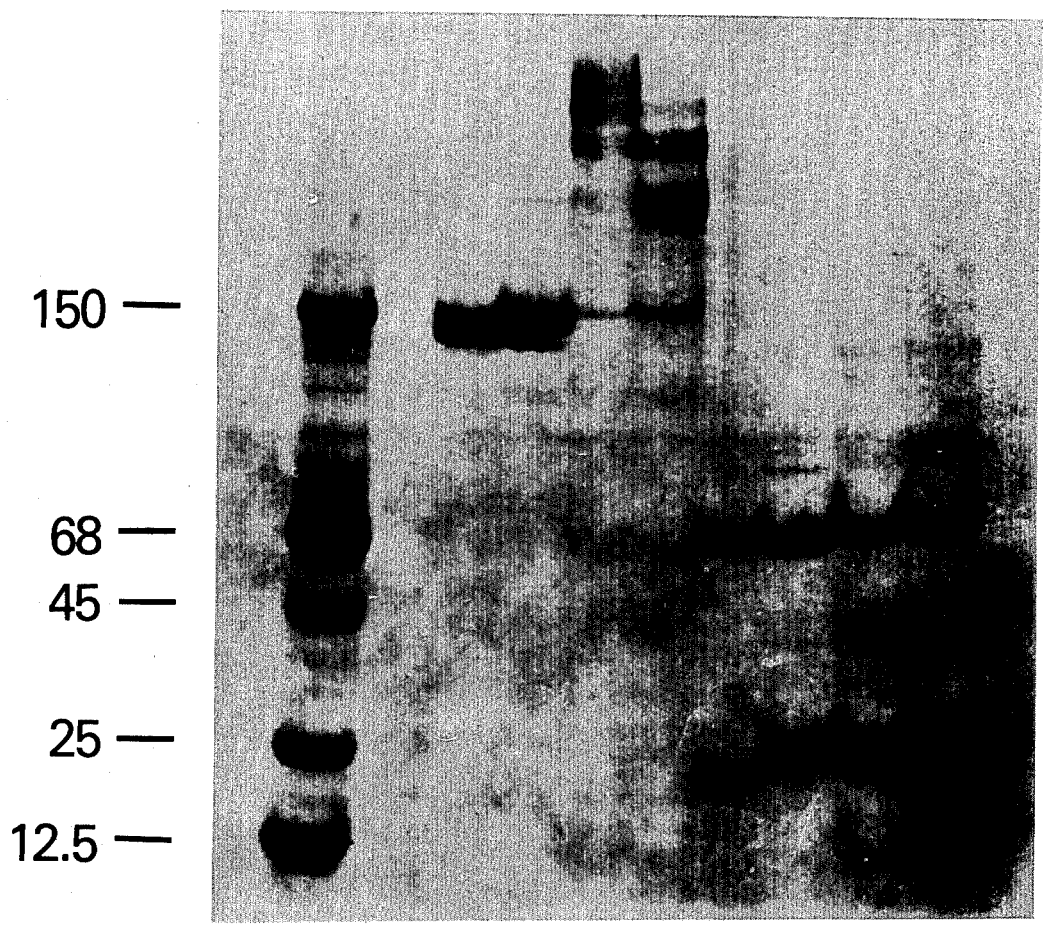

TARGET SPECIFIC CROSS-LINKED HETEROANTIBODIES

BACKGROUND OF THE INVENTION

1. Technical Field

The present invention is related generally to the field of immunochemistry. More particularly, the present invention is related to antibody heteroaggregates which cause normal cytotoxic cells to attack specifically targeted cell types.

2. State of the Art

The most widely used methods for eliminating pathogenic or otherwise undesired cells is through the use of drugs. In most cases, however, drugs are not totally specific for the target, and serious side effects result. This is especially true for anti-cancer agents which are highly toxic for normal cells and produce severe adverse reactions. Moreover many types of neoplasms are unresponsive to chemotherapy. Similarly anti-viral or immunosuppresive drugs also often exhibit many side effects.

One of the methods for obtaining increased specificity is through the use of target-specific antibodies, especially monoclonal antibodies. Such antibodies can, through their antibody binding sites, bind specifically to a designated target cell, for example a virally-infected cell, a tumor cell, a parasite, or a particular type of normal cell which expresses a distinctive cell surface antigen. However, the mere binding of antibodies to cells does not always lead to their destruction. Therefore, attempts have been made to render the antibodies cytotoxic by attaching a drug, toxin or radiolabelled isotope to them. Such "magic bullets", are under intense investigation. However, in many cases the antibody conjugates do not reach the target tissue because they are cleared rapidly from the circulation. Moreover, often large amount of antibodies must be injected and when they are taken up non-specifically by the wrong cells, serious side effects can result. Because of such limitations, a better method for destroying unwanted cells in vivo is needed.

SUMMARY OF THE INVENTION

It is, therefore, an object of the present invention to provide a means by which elements of the immune system can be targeted against specific types of unwanted or detrimental cells.

It is a further object of the present invention to provide cross-linked antibodies capable of directing normal immune system to attack specific targets in vivo.

It is yet another object of the present invention to provide a method of producing cross-linked heteroantibodies capable of causing normal cytotoxic cells to inactivate a specific cell type.

It is an additional object of the present invention to provide antibody heteroaggregates which cause antibody-dependent cell-mediated cytolytic (ADCC) effector cells and cytotoxic T cells (CTL) to specifically lyse designated cell types.

An advantage of the present procedure over other known procedures is that it utilizes an individual's own cellular immune mechanisms to render a variety of undesirable cells non-functional. Furthermore, unlike other antibody-dependent therapies, small amounts of cross linked antibody will provoke a relatively large cytotoxic response against pathogenic target cells because effector cells which have been treated with the cross-linked antibody can kill multiple target cells. Therefore, the possibilities of adverse side effects due to antibody cross reactivities, contaminants in the antibody preparations, and reactions against antibodies of the host are minimized. In the current invention, the specificity of lysis depends only upon the specificity of the anti-target antibody. Hence, as long as there is an anti-target antibody available, the efficacy and utility of the present system is unlimited.

Additionally, the technique of the present invention does not introduce toxins, drugs, radioactive material and the like into the body. Rather, it activates the body's own immune system to attack the undesirable, harmful or pathogenic entity, thereby eliminating such deleterious entities by lysing or by rendering them functionally ineffective.

Other objects and advantages will become evident as the detailed description of the present invention proceeds.

BRIEF DESCRIPTION OF DRAWINGS

These and other objects, features and many of the attendant advantages of the invention will be better understood upon a reading of the following detailed description when considered in connection with the accompanying drawing wherein:

FIG. 1 demonstrates that the procedure described below yields covalently cross linked antibody heteroaggregates. This is shown for one particular combination of IgG antibodies, anti-T3 cross linked to anti-H2K$^k$. FIG. 1 is a polyacrylamide electrophoretic gel of monomeric (starting material) and cross linked antibodies in the presence of the ionic detergent, sodium dodecylsulfate. Lanes 1 and 2 are the unlinked monoclonal antibodies, anti-T3 and anti-H-2K$^k$, respectively. Lanes 3 and 4 are two fractions of the hetero-cross linked antibodies separated by size by gel filtration. Lane 3 is the heavier fraction consisting mainly of trimers, tetramers, and pentamers. Lane 4 is the lighter fraction and is mainly dimers and trimers. Lanes 5-8 are the same as lanes 1-4 except that disulfide bonds have been reduced. Because the antibodies were cross linked with a reducible cross linking reagent, only immunoglobulin heavy and light chains are observed after reduction in lanes 7 and 8.

DETAILED DESCRIPTION OF INVENTION

These and other objects and advantages of the present invention are achieved by target specific cross-linked heteroantibody and a method of producing the same.

The various terms as used herein are defined as follows.

The term "heteroantibody" or "antibody heteroaggregate" means two or more cross-linked, dissimilar antibodies one of which is directed against a specific receptor entity on a cytotoxic cell and the other is directed against a cell surface component on the target cell. These antibody heteroaggregates can also be designated as "antibody 1 x antibody 2", for example anti-T3×anti-K$^k$.

The term "target cell(s)" means those cells which are undesirable and need to be eliminated, attacked and/or destroyed functionally or otherwise. "Target specific" means directed against specific target cells.

All other terms have the same meaning as is well established in the scientific literature or as is generally understood by those of ordinary skill in the art.

Some of the essential features of this invention are:

(1) That one of the antibodies be directed against the receptor (or receptor complex) on the cytotoxic effector cell which is responsible for triggering lysis. Antibodies against other cell surface components may not work.

(2) That the second antibody be directed against a cell surface component on the target cell which needs to be destroyed. The target cell surface component must be in sufficiently high density to trigger lysis, and should not be present in secreted form in solution, as this may block the interaction of the effector cell with the target.

(3) The two antibodies must be physically cross-linked to one another.

Although any type of effector or cytotoxic cells could be used, the preferred effector cells particularly suitable for the present invention are those which belong to the two main classes of cytotoxic cells: (a) antibody-dependent cytolytic cells (ADCC effector cells); and (b) cytotoxic T cells (CTL). Cells belonging to ADCC and CTL categories normally bind the target cell by specific receptors and lyse the target cell. Without being bound to any particular theory, it is postulated that in accordance with the present invention, ADCC effectors bind and lyse antibody-coated target cells, while CTL bind to histocompatibility antigens on the target cells. What the heteroaggregates of the present invention do is to form an artificial bridge or a cross-linkage between the target cell on the one hand and the receptor on the cytotoxic cell on the other. Thus, by simply finding an antibody against the target cell or any part thereof, and incorporating this target-specific antibody as one of the components into the heteroaggregate (the other component of the heteroaggregate being a second antibody specific to the receptor complex or any part thereof on the cytotoxic effector cell), the specificity of lysis by the effector cell can be manipulated so as to be directed against any target cell having an antibody available thereto.

For the purposes of the present invention, any cross linking agent can be utilized. However, it is preferable to use a reagent, such as SPDP vide infra, which only forms heteroaggregates, since homoaggregates will, of course, not retarget the effector cell, and could conceivably block retargeting.

Although any similar or equivalent methods and material can be utilized in the testing and/or practice of the present invention, the preferred methods and materials are now described. All publications mentioned hereunder are incorporated herein by reference. Most of the hybridoma cell lines producing the antibodies used in the following descriptions are obtainable from the American Type Culture Collection (ATCC), Rockville, Md. They can also be obtained from individual investigators. Of course, the antibodies which can be employed in accordance with the present invention can either be monoclonal, polyclonal or a combination of the two.

Materials and Methods

Antibodies

Both monoclonal and polyclonal antibodies are purified by standard laboratory procedures. For example, rabbit anti-2,4-dinitrophenyl (DNP) antibodies were isolated from immune serum by affinity chromatography followed by gel filtration as described by Segal, et al., Biochemistry 15:5253 (1976).

Monoclonal antibodies were grown as ascites in nude mice and isolated by gel filtration and ion-exchange chromatography as described by Unkeless, J. Exp. Med. 150:580 (1979). The precise methods of antibody production and purification are not important as long as pure, antibody is obtained. Polyclonal antibodies must be affinity purified in order for this method to work.

In some instances it is preferable to use immunoglobulin fragments, e.g. Fab or F(ab')$_2$, rather than the intact immunoglobulin.

Fab fragments were prepared by incubating purified antibodies for 4 h at 37° with a 1:100 (wt:wt)ratio of papain to immunoglobulin in 0.1 M sodium phosphate 0.1 M NaCl, lmM EDTA, 20 mM cystein, pH 8.0. The reaction was terminated by adding iodoacetamide to a final concentration of 30 mM. Analysis by SDS-PAGE indicated that the proteins had been completely digested to 50 Kd fragments. They were then dialyzed vs 0.1 M Tris.Cl, pH 8.5 and passed over a protein A-Sepharose column to remove Fc fragments and trace contaminants of intact IgG. F(ab')$_2$ fragments from most monoclonal antibodies can be prepared by pepsin digestion in the pH range of 3.5–4.5, the exact pH required depending upon the antibody being digested (Dower et al, 1984, J. Immunol 132:751).

Cross Linking of Antibodies

Any procedure which forms active antibody heteroaggregates can be employed. Three preferred methods which have been used successfully are now described.

(1) Heteroaggregates were prepared using SPDP (N-succinimidyl-3-(2-pyridyldithiol) propionate) according to the manufacturer's (Pharmacia Fine Chemicals, Pisctaway, N.J.) protocol. The detailed procedure for one prepration was as follows. Rabbit anti-DNP IgG antibodies (2ml, 12 mg/ml) and 2.4G2 (rat anti mouse Fc receptor (Fc$_\gamma$R)) (4.6 ml, 5.2 mg/ml) were each dialyzed against 0.1 M potassium phosphate, 0.1 M NaCl, pH 7.5 (coupling buffer), and incubated separately for 2 h at room temperature with three fold molar excesses of SPDP (47 µl of a 3.2-mg/ml solution of SPDP in ethanol was added to each sample). The 2.4G2 was redialyzed against coupling buffer and the anti-DNP was dialyzed against 0.1 M sodium acetate, 0.1 M NaCl, pH 4.5 (reducing buffer). Dithiothreitol was then added to the anti-DNP to final concentration of 0.02 M. After 30 min at room temperature, the anti-DNP was passed through a Pharmacia PD10 column equilibrated with coupling buffer, and immediately added to the 2.4G2. After 4 h incubation at room temperature, 1 mg of iodoacetamide was added and the protein was eluted on a 2.6×90 cm Ultrogel AcA 22 column in borate buffered saline (BBS) plus 0.02% sodium azide. Polymerized material was collected in two fractions and concentrated using a Millipore CX-10 immersible membrane. This procedure produces a reducible heteroaggregate.

(2) Non-reducible heteroaggregates are produced as follows: 10 mg of each protein was dialyzed against coupling buffer. To one protein was added a 3 fold molar excess of SPDP, to the other a 3 fold molar excess of SMCC (Succinimidyl 4-(N-maleimido-methyl) cyclohexane-1-carboxylate). After 2 hr at room temperature the SPDP-protein was dialyzed against reducing buffer and the SMCC protein against coupling buffer. The SPDP protein was then reduced with 0.02M dithiothreitol for 30 min at room temperature, and dialyzed 3 times, 2 hour each time, against 100 volumes of coupling buffer at 4° C. It was then added to the SMCC-antibody and allowed to react 4 hr at room temperature (23° C.–30° C.). Approximately 50% of the starting material was cross linked. The material was active without fractionation.

(3) The avidin-biotin interaction to produce cross linked antibody is as follows:

(a) Biotin anti-target cell antibody:

Dialyze 1 mg of antibody in 1 ml phosphate buffered saline (PBS) vs 0.1 M NaHCO$_3$ pH 8.7.

Dissolve 1 mg of N-hydroxysuccinimidobiotin (bio-NHS) in 1 ml dimethylsulfoxide. Add 7 ul of bio-NHS solution to protein (a 3 fold molar excess). Let sit 1 hr at room temperature. Dialyze vs PBS.

(b) Avidin anti-receptor antibody

Dialyze 12.5 mg of antibody, and 12.5 mg of avidin vs coupling buffer, each protein in 1 ml volume. Add a 3 fold molar excess of SPDP to the antibody (dissolve 3 mg SPDP in 0.5 ml ethanol, add 13 $\mu$l ). Add 8 fold excess of SPDP (77 $\mu$l ) to avidin. React 1 hr at room temperature. Dialyze avidin vs coupling buffer and antibody vs reducing buffer. Add dithiothreitol to antibody to a final concentration of 0.02 M. React 10 min. at room temperature. Pass the antibody solution through a Pharmacia PD10 column equilibrated with coupling buffer. Add antibody to avidin. React 4 hr at room temperature. Pass cross linked protein on a 1.6×90 cm Ultrogel AcA22 column. Collect and pool material of molecular weight 150,000 or greater.

Bring pH of this material to 10.5 with 0.1 M lysine, pH 11.0. Apply to 3×1 cm iminobiotin-Sepharose column. Wash with 0.1 M lysine, pH 10.5. Elute bound protein with 1 M sodium acetate, pH 4.5. Dialyze eluted protein vs PBS. This is the purified avidin-antibody complex.

To cross link biotin anti-target antibody to avidin anti-receptor, mix the two proteins together at a 2:1 (wt/wt) ratio of biotin-antibody:avidin-antibody, at a total protein concentration of about 1 mg/ml. Add immediately to cells.

Lytic Assays

Effector Cells. Cells from the P388$_1$ mouse macrophage line were grown in spinner culture as described by Koren, et al., J. Immunol. 114:894 (1975), harvested, washed twice, and resuspended to a final concentration of 2–4×10$^7$ cells/ml in culture medium containing the desired concentration (usually 10–20 $\mu$g/ml) of cross-linked antibody. After incubation at 0° C. for 30–45 min, cells were washed twice and resuspended to the desired concentration in culture medium.

Human CTL clones 8.2, 8.4, 8.5 and 8.9 were carried in the laboratory of Dr. Steven Shaw and are specific for the HLA-DPw2 antigen (Biddison, et al., J. Exp. Med 159:783 (1984); Shaw, et al., J. Immunol. 134:3019 (1985)).

Mononuclear cells were isolated from freshly drawn, heparinized veinous blood from normal donors by density gradient separation over Ficoll-Hypaque (LSM, Bionetics, Kensington, MD). Monocytes were depleted by passage over Sephadex G10 as described (Hathcock, et al. (1980) Manual of Macrophage Methodology, Edited by H. B. Herscowitz et al., Marcel Dekker, NY, p.78) yielding a lymphocyte preparation. The leu 11+ cells (including most of the NK activity) were removed from the lymphocytes by incubating them with anti-Leu 11b (Becton-Dickinson, Mountain View CA) and rabbit complement (Pel Freeze, Rogers, AK) using Becton-Dickinson's suggested protocol.

In some experiments, large numbers of cells were obtained from a normal donor by leukapheresis. In those experiments cells were cryopreserved and stored in liquid nitrogen (Holden, et al. (1977) In vitro Methods Cell-Mediated and Tumor Immunity. Ed. by B. R. Bloom and J. R. David. Academic Press New York p. 723) as either mononuclear cells, lymphocytes, or as Leu 11-depleted lymphocytes.

Target Cells

Target cells used in the assays are RDM4 and EL4 which are, respectively, H-2$^k$ and H-2$^b$ murine T-cell lymphomas, and M16 (Shaw et al, J. Exp. Med. 152:565 (1980)) is a human Epstein-Barr virus transformed lymphoblastoid cell line. Chicken red blood cells (CRBC) were also used as targets. In some experiments, target cells were modified with TNP by incubating them with 3 mM trinitrobenzene sulfonate for 10 min at 37° in PBS, pH 7.4. Cells were $^{51}$Cr-labeled as desribed (Jones et al. J. Immunol. 126:2457 (1981). Human tumor cells were obtained from various investigators.

Cytotoxicity Assays

Cytotoxicity was measured in culture medium using 96 well, U-bottom microtiter plates (Jones et al, 1981, J. Immunol. 126:2457). To each well was added varying numbers of effector cells in 100 $\mu$l medium, followed by 20 ul of antibody or medium and either 1×10$^4$ or 5×10$^3$ $^{51}$Cr-labeled target cells in 100 $\mu$l medium. Plates were incubated for 4 hr. at 37° in 5% CO$_2$, 100% humidity. Superatants were harvested with a Titertek harvesting system (Skatron, Sterling, VA), and counted in a well-type gamma counter. Triplicate determinations were made for each sample. Maximum lysis was measured by incubating target cells in 5% Triton X-100, and spontaneous release was determined by incubating the target cells in medium alone. Percent lysis (P) was calculated from the formula:

P=100×(experimental release-spontaneous release)/(maximum release-spontaneous release).

Results

To demonstrate that anti-T3 containing heteroaggregates can cause human T cells to lyse any desired target cells, four different human anti-HLA-DPw2 (SB2) cytotoxic T lymphocyte (CTL) clones 8.2, 8.4, 8.5 and 8.9, were tested. All four express the T3 and T4 antigens and target cell lysis mediated by three of the clones (8.4 being the exception) is inhibited by anti-T3 antibody (Biddison et al, J. Exp. Med. 159:783 (1984)). Clones 8.9 and 8.5 were negative for FC$_{65}$R (as determined by flow cytometry) and therefore cannot mediate ADCC (clones 8.2 and 8.4 were not tested). Cross linked antibodies were prepared as described in the Methods Section. Two cross linked fractions were separated from monomeric IgG by gel filtration (FIG. 1). Tests showed that both were equally active and they were, therefore, used interchangeably.

In Table I, the four clones were tested for the ability to lyse M16, a DPw2+human lymphoblastoid cell line, RDM4, an H-$2^k$ mouse tumor line, and EL-4, an H-$2^b$ mouse tumor line. The data indicate that these clones lyse the M16 target but not the murine tumor cells. Moreover, lysis of M16 by clones 8.9, 8.2 and 8.5 was blocked by anti-T3×anti-$K^k$ showing that anti-T3 remained active in the heteroaggregate. The main finding of Table I is that anti-T3×anti-$K^k$ causes each of the CTL clones to lyse the $K^k$ positive RDM4 targets, but not the $K^b$-expressing EL-4 cells. RDM4 was also lysed if either effector or target cells were preincubated with the heteroaggregates and washed prior to experimentation.

As expected, the antibody heteroaggregates cause a specific increase in conjugates between effector and target cells. Thus, when clone 8.9 and RDM4 were mixed, only 8% of the cells were in conjugates, whereas in the presence of anti-T3×anti-$K^k$, 31% were in conjugates.

TABLE I

Anti-T3 × anti-$K^k$ heteroaggregates retarget CTL to $K^k$-expressing cells

| Clone | anti-T3 × anti-$K^k$ | % Specific lysis of target cell | | |
|---|---|---|---|---|
| | | M16 | RDM4 | EL-4 |
| 8.9 | — | 47.0 | 6.6 | .8 |
| 8.9 | + | 11.5 | 53.3 | .2 |
| 8.2 | — | 44.9 | 9.1 | 3.3 |
| 8.2 | + | 20.4 | 43.9 | −.7 |
| 8.4 | — | 49.8 | 7.2 | 4.3 |
| 8.4 | + | 54.1 | 32.9 | .8 |
| 8.5 | — | 35.7 | 1.5 | .6 |
| 8.5 | + | 8.0 | 30.0 | .4 |

Lysis was measured in the presence or absence of 5 μg/ml anti-T3 × anti-$K^K$ at a 10:1 effector:target ratio in a 3 hr $^{51}$Cr release assay. Antibody was preincubated with effectors and targets for 30 min at 0°, before warming to 37°. Human CTL clones 8.2, 8.4, 8.5 and 8.9 are specific for the HLA-DPw2 antigen. M16 is a human Epstein-Barr Virus-transformed lymphoblastoid cell line which expresses HLA-DPw1 and DPw2 antigens. RDM4 and EL4 are H-$2^k$ and H-$2^b$ murine T-cell tumor lines. Percent lysis was calculated as described in the methods section, and spontaneous release was 8.9, 5.2, and 6.8 percent for M16, RDM4, and EL-4, respectively.

In order to test the specificities required for cross linked antibodies to mediate lysis, anti-T3 was cross linked to anti-DNP, anti-T4 to anti-$K^k$ and anti-DNP to anti-$K^k$. The data in Table II show that the anti-T3×anti-DNP confers anti-DNP specificity to T-cell clones; in the presence of this heteroaggregate, CTL lyse TNP-RDM4 and TNP-EL4 but not unmodified EL4 or RDM4. Moreover, DNP hapten in solution strongly inhibits lysis of the haptenated targets. It is noted that CTL even lyse hapten-modified chicken red blood cells-(CRBC) in the presence of anti-T3×anti-DNP. Thus, the antibody heteroaggregates seem to override the normal requirement for lysis that T-cell receptors bind to histocompatibility antigens on target cells, since it is unlikely that either CRBC or the murine T-cell tumor lines EL4 and RDM4 express histocompatibility antigens which could be recognized by the class II specific CTL clones used here.

TABLE II

The specificity of CTL lysis in the presence of hetero-crosslinked antibodies

% specific lysis of target cells by clone 8.9
Antibody added

| Target | None | anti-T3 × anti-$K^k$ | anti-T3 × anti-$K^k$ + anti-T3 | anti T3 × anti DNP | anti-T3 × anti-DNP + DNP | anti-T4 × anti-$K^k$ |
|---|---|---|---|---|---|---|
| M16 | 37.8 | −7.0 | −29.7 | 22.3 | — | 29.9 |
| RDM4 | −8.7 | 38.2 | 2.0 | −8.6 | — | 2.1 |
| EL-4 | −4.9 | −4.2 | — | −4.3 | — | — |
| CRBC | 1.1 | — | — | 1.3 | .0 | — |
| M16-TNP | 55.1 | — | — | 32.3 | 43.8 | — |
| RDM4-TNP | −8.1 | — | — | 40.5 | 7.4 | — |
| EL-4-TNP | .4 | — | — | 49.1 | .3 | — |
| CRBC-TNP | 0.8 | — | — | 63.9 | .0 | — |

Experiments were performed as described in Table I using clone 8.9 cells as effectors. Clone 8.5 also lysed TNP-CRBC in the presence of anti-T3 × anti-DNP in a hapten-specific manner (data not shown). In all experiments shown in Table II, 10 μg/ml cross linked antibody was used, but 20 and 40 μg/ml of anti-T4 × anti-$K^k$ were also tested with results similar to those shown here. Anti-T3 (50 μg/ml, column 4) and DNP-ε-aminocaproate (0.1 mM, column 6) were used as inhibitors. DNP-ε-aminocaproate did not inhibit lysis of M16 by clone 8.9 (data not shown). Target cells were modified with TNP by incubating them for 10 min at 37° in PBS, pH 7.4, containing 3 mM trinitrobenzene sulfonate. — indicates experiment not done. Negative values for percent lysis indicate that chromium release was less than spontaneous release. In the test sample, spontaneous release values for the various targets were: M16, 28.6%; RDM4, 11.4%; EL-4, 12.4%; CRBC, 2.9%; M16-TNP, 7.4%; RDM4-TNP, 15.4%; EL-TNP, 4.5% AND CRBC-TNP, 3.0%.

It was important to establish if anti-T3 was a necessary component of the antibody heteroaggregate, or if mAb against any effector cell surface molecule would trigger lysis. Therefore, the effect of anti-T4×anti-$K^k$ upon lysis of M16 and RDM4 was tested. In the presence of anti-T4×anti-$K^k$, 21% of effectors were conjugated while 9% were conjugated in its absence. However, as shown in Table II, this cross linked preparation neither promoted lysis of RDM4 nor significantly blocked lysis of M16 by clone 8.9. In a second test CTL clone 8.9 was treated with 1.5 mM trinitrobenzene sulfonate and tested for lysis against RDM4 in the presence of anti-DNP×anti-$K^k$. Control experiments showed that anti-DNP×anti-$K^k$ promoted specific conjugate formation between TNP-8.9 and RDM4 and that the TNP-8.9 cells were able to lyse their natural target, M16. However, TNP-8.9 cells did not lyse RDM4 cells in the presence of anti-DNP×anti-$K^k$ (<2% lysis over a concentration range of 5–40 μg/ml heteroaggregate). Therefore, cross linking of target cells specifically to the T4 molecule and to a presumably large number of TNP-modified components on the effector cells did not lead to lysis. These data suggest that the cross linking of target cells directly to the T-cell receptor complex is a requirement for lysis.

Lysis of Target Cells by Peripheral Blood T Cells

In order to show that freshly drawn human peripheral blood T cells could also be rendered cytotoxic for specified targets with appropriate cross linked antibodies, mononuclear cells were incubated with $^{51}$Cr-labeled RDM4 in the presence of anti-T3 x anti-$K^k$ or with $^{51}$Cr-labeled TNP-RDM4 in the presence of anti-T3 x anti-DNP (Table III): In both cases, the mononuclear cells lysed the target cells when cross linked antibody was present, but did not mediate lysis in the absence of antibody. However, mononuclear cells also mediated antibody-dependent cellular cytotoxicity (ADCC), as shown by target cell lysis in the presence of anti-K$^k$ (which is an IgG2a antibody). Since the cross linked antibodies possessed Fc fragments, it was possible that tumor cell lysis in the presence of the antibody heteroaggregate represented ADCC and not heteroaggregate-dependent lysis mediated by peripheral blood T cells. To eliminate this possibility, mononuclear cells were first passed over Sephadex G10 to remove monocytes. This removed approximately ⅔ of the OKM1+ cells, and essentially all of the cells falling within the OKM1 bright peak. As a result of monocyte depletion, ADCC activity was substantially reduced, while heteroaggregatedependent lysis increased (Table III). An aliquot of the G10-passed cells was then treated with anti-leu 11b and complement, to remove the K, NK subset of cells. (The Leu 11 epitope is on the neutrophil and K cell Fc$\gamma$ receptor, but not on monocyte Fc$\gamma$ receptors (Perussia et al., J. Immunol. 133:180 (1984)). This treatment removed the reamining ADCC activity, (Table III) leaving a population of lymphocytes which was 87% T3+ and which required the anti-T3-containing heteroaggregate for mediating lysis.

TABLE III

| | | Lysis of RDM4 Cells by Franked Peripheral Blood T Cells | | | |
|---|---|---|---|---|---|
| | | Effectors | | | |
| Exp | Antibody | Mononuclear Cells | Monocyte depleted$^c$ (lymphocytes) | Leu 11 depleted lymphocytes$^d$ | IL-2$^e$ activated |
| | | | % lysis | | |
| 1$^a$ | none | −0.6 | 1.8 | −0.3 | 4.6 |
| | anti-T3 × anti-K$^k$ | 10.1 | 16.2 | 26.0 | 43.2 |
| | anti-K$^k$ | 18.5 | 8.4 | −2.3 | 3.9 |
| 2$^b$ | none | −1.8 | −1.0 | −1.4 | 3.1 |
| | anti-T3 × anti-DNP | 6.2 | 7.5 | 8.4 | 38.2 |
| | anti-K$^k$ | 5.7 | 2.1 | 0.0 | 2.6 |

$^a$Tested against $^{51}$Cr-labeled RDM4 at E:T = 20:1 in a 4 h assay. Anti-T3 × anti-K$^k$ and anti-K$^k$ were added to wells at 10 μg/ml and 5 μg/ml final concentrations, respectively. Anti-K$^k$ is 36-7-5, a mouse IgG2$_a$ monoclonal antibody.
$^b$Same as in exp 1 except targets were TNP-RDM4 and anti-T3 × anti-DNP was used at 5 μg/ml. Effector cells were from a different donor than in exp 1.
$^c$By passage over Sephadex G10.
$^d$By treatment of the G10-passed cells with anti-Leu 11b and complement.
$^e$Leu 11 depleted lymphocytes were incubated overnight with 50 (exp 1) or 30 (exp 2) units/ml of recombinant IL-2.

The data of Table III show that heteraggregate-dependent lysis mediated by human peripheral blood T-cells is markedly enhanced by overnight incubation with recombinant IL-2. Other data indicated that unlike IL-2, recombinant human interferon does not stimulate lysis.

Retention of heteroaggregate-dependent Lytic activity by human T cells

It was also important to determine for in vivo use of heteroaggregate-treated T cells, as to how long after treatment did the T cells retain activity when incubated at 37°, the physiological temperature. To test this, Leu 11-lymphocytes were activated with IL-2 and divided into two portions, one of which was incubated with anti-T3×anti-K$^k$, the other with medium alone. The cells were then washed and incubated for 0, 4, 8, or 24 hr at 37° and tested for lytic actvity against RDM4. As seen in Table IV, the treated cells retained considerable activity even after 24 hr incubation.

Lysis of Human Tumor Cells by T-cells treated with Anti-T3×anti-tumor cell

It has been deomonstrated above that cloned human CTL or human peripheral blood T cells can be induced, in vitro, to lyse target cells, which they normally would not lyse, by treating them with certain covalently cross-linked antibody heteroaggregates. In order to demonstrate that such effector cells can also be used to lyse tumor cells, several anti-tumor monoclonal antibodies were cross linked to anti-T3. The data presented below show that these heteroaggregate preparations cause human peripheral blood T cells to specifically lyse cultured tumor cells and fresh human tumor cells, but not normal cells from a variety of tissues.

TABLE IV

| Effector Cells Retain Activity During Incubation at 37° C. | | | | | |
|---|---|---|---|---|---|
| Treatment with | | Time of Incubation (hr) at 37° C. | | | |
| Heteroaggregate$^b$ Pre-coat$^c$ | In medium$^d$ | 0 | 4 | 8 | 24 |
| | | Percent Specific Lysis (lytic units)$^a$ | | | |
| − | − | 2.2 | 3.7 | 4.5 | 6.5 |
| − | + | 33.7 (5.3) | 51.4 (7.4) | 42.4 (4.4) | 21.9 (1.3) |
| + | − | 33.0 (4.3) | 46.6 (4.3) | 48.5 (5.0) | 31.4 (2.4) |
| + | + | 32.0 (5.6) | 44.3 (3.9) | 49.2 (3.9) | 21.4 (1.4) |

$^a$Percent lysis of RDM4 cells by IL-2 activated, Leu 11$^−$ lymphocytes at E:T = 20:1. Lytic units, defined as the initial slope of a hyperbolic fit to the E:T dose response curve, are indicated in parentheses, where measurable. Effector cells were activated by overnight incubation with incubation with 100 units/ml recombinant IL-2.
$^b$Anti-T3 × anti-K$^k$
$^c$Effector cells were incubated 1 hr. at 0° C. with (+) or without (−) 20 μg/ml heteroaggregate and washed, prior to incubation at 37° C.
$^d$Heteroaggregate (5 μg/ml) was either present (+) or absent (−) in the lytic assay medium.

Human CTL clone 8.9 was treated with three different heteroaggregates and tested for lysis against various human tumor lines (Table V). Also shown in Table V are the results of fluorescence analyses of cells which were stained with the anti-tumor antibodies. Antibody 315F6, which was raised against a large cell lung carcinoma, binds to all of the tumor lines tested and, when crosslinked to T3, promotes lysis of all of the tumor lines by clone 8.9. Antibody 8H12 (anti-breast cancer) cross-reacts on small cell lung cancer and colon cancer lines and promotes their lysis, while HeFi-1 binds specifically to the L428 Reed-Sternberg Line, against which it was raised, and promotes lysis of that line when crosslinked to anti-T3. Thus, heteroaggregates containing anti-tumor antibodies can direct clone 8.9 to lyse human tumor targets, and the specificity of lysis parallels the specificity of the anti-tumor antibody.

Having demonstrated that heteroaggregate-treated cloned CTL can lyse tumor lines, it was next determined that treated human peripheral blood T cells could lyse cells from either fresh tumor tissue or fresh normal tissue. Table VI shows that peripheral T cells treated with anti-T3 crosslinked to several anti-tumor antibodies specifically lyse fresh tumor cells but, with the exception of liver, do not lyse normal cells. Of the tumor cells that were tested, melanoma and colon cells were observed to be the most susceptible to lysis. It is not known with certainty why normal liver cells are lysed to a small extent by the treated T cells, but if some of the liver cells express Fc receptors, then they might bind to the T cells by the Fc portions of the heteroaggregates, rather than by the antibody combining sites. This could be prevented by using Fab fragments in the heteroaggregates.

Lysis Mediated by Heteroaggregate-coated ADCC Effector Cells

Initial studies (Karpovsky et al, 1984, J. Exp. Med. 160:1686) showed that mouse ADCC effector cells could be rendered cytotoxic with heteroaggregates containing antibodies against Fc receptors on the effector cells. Typical results from these studies are shown in Table VII. Here cells from a mouse macrophage line were coated with anti-Fc$_\gamma$R $\times$ anti-DNP, and tested for lysis against $^{51}$Cr-labeled chicken red blood cells as targets. Table VII shows that this heteroaggregate causes the effector cells to specifically lyse TNP-modified but not unmodified chicken red blood cells. Untreated effector cells will lyse antibody-coated target cells (Table VII, classical ADCC) but not TNP-CRBC. Unlike classical ADCC, lysis mediated by effectors coated with heteroaggregates is not blockable by immune complexes. For example, in one test, 10 µg/ml of

TABLE V

Heteroaggregate-dependent lysis of human tumor lines by cloned cytotoxic T cells[a].

| Target cells[c] | Heteroaggregate[b] | | | |
|---|---|---|---|---|
| | None | Anti-T3 × 315F6 | Anti-T3 × 8H12 | Anti-T3 × HeFi-1 |
| | Percent specific lysis (mean fluorescent channel × $10^{-2}$)[d] | | | |
| BL-1 | 15 (1.3) | 96 (6.9) | 5 (1.4) | 9 |
| L428 | 6 (1.4) | 90 (5.9) | 15 | 57 (5.0) |
| N592 | 11 (1.3) | 85 (5.5) | 67 (4.9) | 16 |
| N526 | 18 (1.2) | 69 (6.5) | 70 (3.8) | 10 |
| H125 | 9 (1.3) | 42 (4.3) | 14 | 12 |
| LS174T | 2 (1.3) | 69 (5.8) | 53 (4.6) | 12 |
| A549 | 1 (2.5) | 50 (6.1) | 2 (2.5) | 1 |

[a]The human anti-DPW2 Tc clone, 8.9 was incubated with 20 ug/ml crosslinked antibody, washed, and tested for lysis against various target cells at an effector:target ratio of 5:1 in a 4-hour $^{51}$Cr release assay.
[b]Anti-T3 was crosslinked to anti-tumor antibody as described in the methods. Preparations containing mainly dimers, trimers, and tetramers were used. 315F6 was a mouse monoclonal antibody (mAb) raised against a human large cell lung cancer line, the 8H12 mAb was generated against the MCF-7 human breast carcinoma line, and mAb HeFi-1 was raised against the L428 Reed-Sternberg line.
[c]Target cells used in this table are: BL-1, a B-lymphoblastoid line; L428, a Reed-Sternberg line; N592 and N526, small cell lung cancer lines; H125, a large cell lung cancer line; LS174T, a colon line; and A549, a lung carcinoma line.
[d]Tumor cells were incubated with biotinylated 315F6, 8H12, HeFi-1 for 30 minutes on ice. Cells were washed, resuspended in 10 ul of 50 ug/ml fluorescein isothiocyanate-avidin, and incubated for 15 minutes on ice. The cells were washed and analyzed by flow cytometry. Mean log fluorescence is indicated with 100 channels corresponding to a factor of 2 increase in fluorescence (e.g., 315F6 stains BL-1 with fluorescences about 50-fold over background).

immune complexes inhibited classical ADCC by over 80% while inhibition of heteroaggregate-dependent lysis was undetectible (Karpovsky et al, 1984, J. Exp. Med. 160:1686).

TABLE VI

Lysis of fresh human normal and neoplastic tissue by heteroaggregate-treated peripheral blood T cells[a].

| Heteroaggregates[c] | Target tissue[b] | | | | | |
|---|---|---|---|---|---|---|
| | Melanoma | Lung cancer | Normal lung | Colon tumor | Normal liver | Normal kidney |
| | Percent specific lysis | | | | | |
| none | 1 | 9 | 1 | 1 | −1 | 3 |
| anti-T3 × 96.5 | 24 | 4 | −3 | −1 | 9 | 2 |
| anti-T3 × 315F6 | 30 | 4 | 2 | 16 | 10 | 4 |
| anti-T3 × 8H12 | −1 | 7 | 3 | 41 | 8 | 1 |
| anti-T3 × 47D10 | 2 | 5 | −1 | 18 | 10 | 0 |

[a]Effector cells were prepared as described in the methods, incubated with 10 µg/ml heteroaggregate, and tested for lysis against target cells at a 10:1 effector:target ratio in a 3-hour $^{51}$Cr release assay.
[b]Single cell suspensions were prepared from fresh normal or neoplastic tissue. They were labeled with $^{51}$Cr by adding 0.2 µl $^{51}$Cr stock to 0.5 ml of cells, incubating 4 hours at 37° C., and washing.
[c]96.5 is an anti-melanoma mAb, and 47D10 is an anti-lung carcinoma mAb with crossreactivity against colon tumors.

TABLE VII

Lysis of Target Cells by P388D₁ Cells*

| Treatment of effector cells | Experiment | Percent lysis[++] of: Antibody-coated TNP CRBC | TNP CRBC | CRBC |
|---|---|---|---|---|
| Incubated with medium only | 1 | 12.2 (0.5) | −0.1 (4.1) | −0.5 (0.4) |
|  | 2 | 34.5 (1.0) | 2.5 (0.5) | 0.4 (0.4) |
|  | 3 | 13.8 (1.1) | 3.0 (0.9) | 2.9 (0.6) |
|  | 4 | 11.1 (1.4) | 2.4 (0.1) | −0.6 (0.7) |
|  | 5 | 31.4 (5.7) | 3.5 (0.6) | 1.2 (0.3) |
| Franked with anti-FcγR × anti DNP | 1 | 50.4 (2.4) | 44.5 (5.7) | −0.8 (0.4) |
|  | 2 | 46.3 (3.8) | 34.8 (2.3) | 1.5 (0.5) |
|  | 3 | 107.5 (2.8) | 90.8 (1.6) | −0.1 (0.5) |
|  | 4 | 40.5 (5.5) | 53.3 (2.8) | −0.9 (0.5) |
|  | 5 | 62.7 (3.6) | 49.5 (2.1) | 0.9 (0.2) |

*At effector-to-target ratios of 10:1.
[++]Means of triplicate samples followed by standard errors in parenthesis.
P388D₁ cells were treated with 10 ug/ml of anti-FcγR × anti-DNP.

The data shown in Table VIII demonstrate that human peripheral blood lymphocytes contain a subset of cells which will mediate lysis of TNP-modified EL-4 tumor cells when coated with anti-Fc$_\gamma$R × anti-DNP. These cells are clearly different from the cytotoxic T cells which mediate lysis when coated with anti-T3 × anti-DNP, since removal of the T8+ lymphocytes totally removes all of the T3-dependent activity but only partially removes the Fc$_\gamma$R-dependent lysis, while removal of the Leu 11+ cells does the opposite. The data of Table VIII show that two different kinds of effector cells can be retargeted with appropriate antibody heteroaggregates and indicate that other types of cytotoxic effector cells could also be rendered lytic for designated target cells by using appropriate antibody heteroaggregates. The data in Table VIII also show that cross-linked Fab fragments are as effective as cross-linked intact antibodies in retargeting effector cells. This is important because it may be preferable to use the Fab-containing heteroaggregates for some in vivo applications.

TABLE VIII

Heteroaggregate-dependent Lysis Mediated by Human Peripheral Blood T Cells and ADCC Effector Cells

| Effector Cells | Effector Target Ratio | no antibody | anti-T3(Fab) × anti-DNP(Fab) | anti-FcγR(Fab) × anti-DNP(Fab) |
|---|---|---|---|---|
|  |  |  | % Specific lysis of El-4-TNP |  |
| Lymphocytes | 20 | 3.5 | 39.8 | 81.6 |
|  | 10 | 4.8 | 20.0 | 62.3 |
|  | 5 | 3.9 | 13.7 | 39.5 |
|  | 2.5 | 6.6 | 9.1 | 28.2 |
| Lymphocytes, T8 depleted | 20 | 9.4 | 6.2 | 43.5 |
|  | 10 | 8.1 | 5.5 | 47.8 |
|  | 5 | 6.2 | 4.6 | 35.0 |
|  | 2.5 | 6.0 | 3.7 | 21.9 |
| Lymphocytes, Leu 11 depleted | 20 | 3.7 | 36.7 | 7.8 |
|  | 10 | 3.0 | 19.5 | 4.5 |
|  | 5 | 2.6 | 11.1 | 3.7 |
|  | 2.5 | 4.6 | 6.9 | 2.3 |

Based on the present disclosure, it should be obvious to one of ordinary skill in the art that a multiplicity of cells from freshly drawn human peripheral blood such as granulocytes, monocytes, macrophages, K cells, T cells, and the like could be retargeted by this technique. In other words, many types of cytolytic cell can be targeted to destroy most types of cells using a suitable antibody heteroaggregate as described herein. Some of the examples of the target cells are tumor cells, virally infected cells, fungi, bacteria and parasites, unwanted normal cells such as autoreactive cells, and cells responsible for graft rejection. Tables I-VIII demonstrate the results obtained with cloned and peripheral blood T cells in accordance with the present invention.

For in vivo use of the invention, many protocols could be adopted, depending upon the particular application. For example, normal peripheral blood leukocytes could be removed from a patient, incubated with appropriate antibody heteroaggregates, optionally with an activator such as IL-2, washed, and reintroduced into the circulation. If the treated cytotoxic cells eventually reached the target cells, they could initiate target cell destruction. This procedure renders an extremely efficient use of the antibody. For example $10^9$ human T cells, each with $10^5$ T3 molecules on its surface would bind a maximum of 50 μgm of heteroaggregate. Thus, only microgram amounts of antibody heteroaggregates would be required to retarget a large number of effector cells, and in addition, the heteroaggregates would not be free in the blood where they might be removed by elements of the reticuloendothelial system. Other techniques usually require much higher amounts of antibody, and the antibodies themselves are usually recognized as being foreign and are rapidly removed from the circulation.

Further applications of target-specific heteroantibodies produced in accordance with the present invention for the treatment or control of abnormal conditions, the origin of which may be related, directly or indirectly to abnormal cellular function, are unlimited. As pointed out herein supra, the only requirements are that one of the antibodies be directed against the appropriate receptor on the cytotoxic effector cell and a second antibody be directed against a cell surface component on the target cell and the two antibodies be cross-linked.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. Cross-linked antibody heteroaggregates wherein one antibody of the heteroaggregate binds specifically with a receptor entity on a cytotoxic cell and a second antibody of the heteroaggregate binds specifically with a surface entity on a cell different from and to be lysed by the cytotoxic cell.

2. The antibody heteroaggregate of claim 1 wherein said cytotoxic cell is selected from the group consisting of antibody-dependent cytolytic cell and cytotoxic T lymphocytes.

3. The antibody heteroaggregate of claim 2, wherein the antibodies are cross-linked by avidin coupled to one antibody and biotin coupled to the second antibody.

4. A method of destroying target cells in a mammalian host comprising administering to said host cytolytic amount of cross-linked heteroantibodies.

5. A method of producing target specific heteroantibodies comprising cross-linking a first antibody directed against a receptor entity on a cytotoxic cell with a second antibody directed against a surface component of a target cell.

6. The method according to claim 5 of cross-linking the first antibody to the second by coupling one antibody with avidin and the second antibody with biotin.

* * * * *